United States Patent [19]

Keil et al.

[11] Patent Number: 5,722,772

[45] Date of Patent: Mar. 3, 1998

[54] QUENCH COOLING EFFECTIVENESS APPARATUS FOR CONTINOUS MONITORING

[76] Inventors: Gary D. Keil, R.R. 2, Elmwood, Ill. 91529-9802; Wayne A. Supak, 406 Georgia Pkwy., Washington, Ill. 61571-1042; Sheryl A. Tipton, 109 Arrowhead Ct., East Peoria, Ill. 61611-1808

[21] Appl. No.: 584,029

[22] Filed: Jan. 11, 1996

[51] Int. Cl.⁶ .................................................. G01N 25/00
[52] U.S. Cl. ........................................ 374/45; 374/164
[58] Field of Search ........................... 374/16, 43, 45, 374/57, 133, 164, 183, 185, 208

[56] References Cited

U.S. PATENT DOCUMENTS

| | | | |
|---|---|---|---|
| 2,016,660 | 10/1935 | Weeks | 374/43 |
| 2,587,622 | 3/1952 | Jaffe | 374/43 |
| 3,317,822 | 5/1967 | Watson | 374/43 |
| 4,453,835 | 6/1984 | Clawson et al. | 374/185 |
| 4,498,337 | 2/1985 | Gruner | 374/185 |
| 5,137,370 | 8/1992 | McCulloch et al. | 374/164 |
| 5,151,574 | 9/1992 | Urban | 374/185 |
| 5,221,916 | 6/1993 | McQueen | 374/183 |
| 5,601,363 | 2/1997 | Keil et al. | 374/45 |

*Primary Examiner*—G. Bradley Bennett
*Attorney, Agent, or Firm*—R. Carl Wilbur

[57] ABSTRACT

A quench cooling effectiveness apparatus for continuous monitoring of a heat treat quench system and method of operation is provided. The apparatus preferably includes first and second heat conductive sheaths having temperature sensors installed therein. The heat conductive sheaths are thermally insulated from each other with a heat resistive sheath. A microprocessor is preferably connected to said sensors, applies a known current to one sensor, and calculates a cooling effectiveness of the heat treat quench system from the temperature of the two sensors and the known applied current.

27 Claims, 3 Drawing Sheets

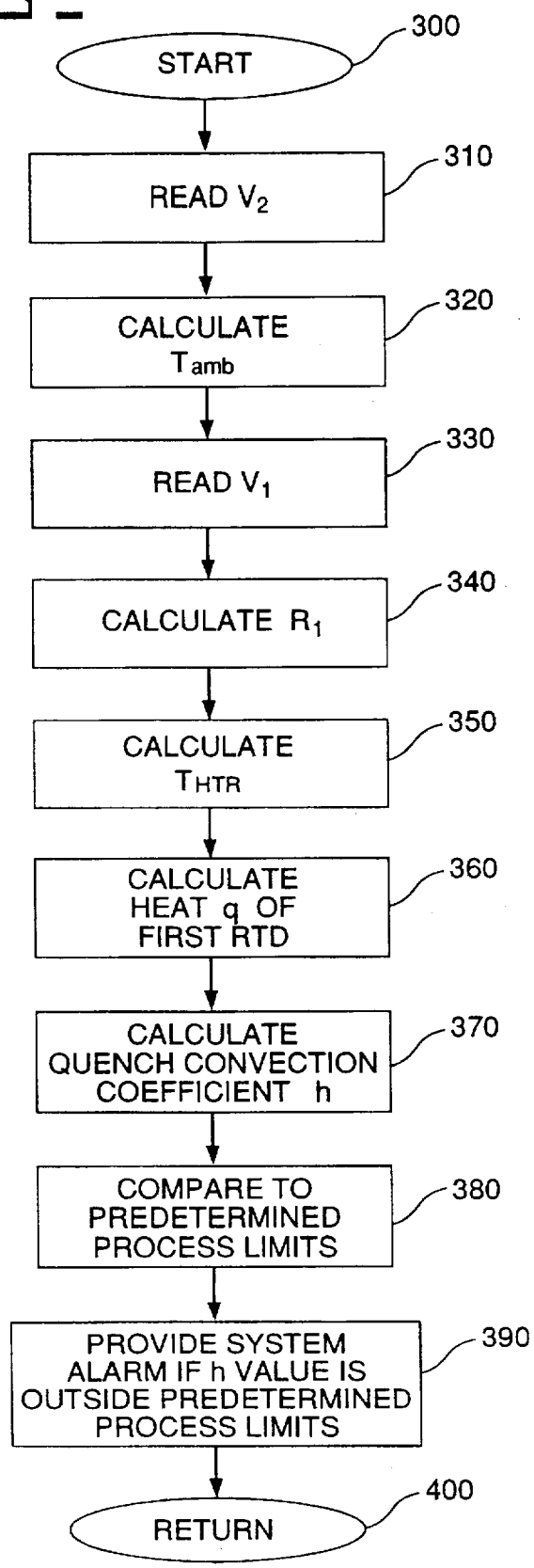

QUENCH COOLING EFFECTIVENESS APPARATUS FOR CONTINOUS MONITORING

TECHNICAL FIELD OF THE INVENTION

The present invention relates generally to devices for measuring the effectiveness of a heat treat quench, and more particularly, to a real time quench probe that can be used as a monitoring and fault detection device, or as a sensor in a closed loop control of the heat treat quench or a quench system.

BACKGROUND OF THE INVENTION

When articles such as metal parts are formed, it is sometimes desirable to harden the parts to improve durability and wear characteristics. One way to harden the part is to immerse the part in a quench immediately after heating the part to the desired temperature. Many different types of media can be used in the quench system, including oil or water, or aqueous polymer solutions, depending on a variety of factors including the material from which the part is made and the desired hardness and microstructural characteristics of the part.

It is desirable for the quench system to provide uniform cooling and for the cooling to be repeatable. Nonuniform cooling can result in varying degrees of hardness, quench cracks, increased distortion and other problems. There are many factors that contribute to non-uniformity of cooling within the quench system. These may include the tank shape and depth, agitation method (i.e, pumps, impellers, agitators, etc.), design and use of flow directing baffles, flow rates within the system, the particular quench media used, and impurities in the system. Typically, to determine the effectiveness or cooling power of a particular quench system and to determine whether one or more of the above fault conditions are present, it has been necessary to quench one or more parts or samples in various areas of the quench system, then cut these parts at one and sometimes several sections to thoroughly analyze hardness and microstructure. However, this procedure is extremely labor intensive and destroys what might otherwise have been a usable part. Moreover, the test only determines the effectiveness at one point in time. It cannot actively monitor the effectiveness of a quench system.

It would be desirable to have a quench system that could continuously monitor the effectiveness and integrity of a quench system during operation and would provide a signal if a condition existed that significantly degraded or increased quench effectiveness. It would also be desirable to have a quench monitor that could be used as an input in a closed loop feedback system to maintain the quench system effectiveness at a desired level by controlling quench system parameters.

There is one type of quench cooling effectiveness apparatus known in the prior art. That type of apparatus is generally disclosed in U.S. Pat. No. 4,563,097 (hereinafter referred to as "the '097 patent"), entitled "Method of Evaluating Cooling Performance of Heat Treatment Agent And Apparatus Therefor". The '097 patent discloses an apparatus having a single resistance temperature detector ("RTD"). This apparatus applies varying current levels to the RTD which causes the RTD to be heated to different temperature levels. Because a temperature/resistance relationship is known for the RTD, the apparatus can determine the RTD temperature as a function of the voltage applied to the RTD and a measured current through the RTD.

In the '097 patent, the RTD sensor is installed into a quench system and the RTD temperature is varied to produce a dissipated heat v. temperature curve for that particular quench media. The effectiveness of different quench media can thereby be analyzed as a function of a temperature curve. As shown in FIG. 5 of the '097 patent, a quench with strong agitation will have a different cooling curve than that with weak or no agitation.

However, an apparatus such as that disclosed in the '097 patent suffers from several disadvantages. For example, the sensor itself is repeatedly heated (to relatively hot temperatures about 750 degrees C.) and cooled to simulate the cooling of actual parts. The repeated heating and cooling of the sensor causes the sensor to have a short life span and thereby prevents continuous monitoring of the quench system.

There is still another disadvantage associated with the device disclosed in the '097 patent. Because there is only one RTD sensor, both ambient temperature and heated temperature (as measured by the sensor) are not concurrently measured, and therefore ambient temperature changes are not detected. Because ambient temperature is not measured, this device cannot make an instantaneous heat convention measurement and cannot be used for instantaneous monitoring.

The present invention is directed toward overcoming one or more of the disadvantages associated with the prior art quench cooling effectiveness apparatus.

SUMMARY OF THE INVENTION

In one aspect of the present invention an apparatus for measuring the cooling effectiveness of a quench is disclosed. The apparatus includes first and second heat conductive sheaths having temperature sensors installed therein. The first and second sheaths are separated by a heat resistive sheath, which thermally insulates the first heat sheath from the second heat sheath.

In another aspect of the present invention, a method of operating an apparatus for monitoring the effectiveness of a quench is disclosed. The method includes the steps of measuring the resistance of a first and second resistance temperature sensor, applying a known electrical current to the first sensor, calculating a heat output of the first sensor, and calculating a convection coefficient of said quench.

Other aspects and advantages of the present invention will be apparent to those skilled in the art upon reading the detailed description of the preferred embodiment in connection with the drawings and appended claims.

BRIEF DESCRIPTION OF THE FIGURES

Throughout the drawings and the description of the invention, where appropriate, like reference numerals are used to refer to like parts. In the drawings:

FIG. 3 generally shows a flow chart of a preferred embodiment of the software control used in connection with an aspect of the present invention.

DETAILED DESCRIPTION OF A PREFERRED EMBODIMENT

Figure 1:
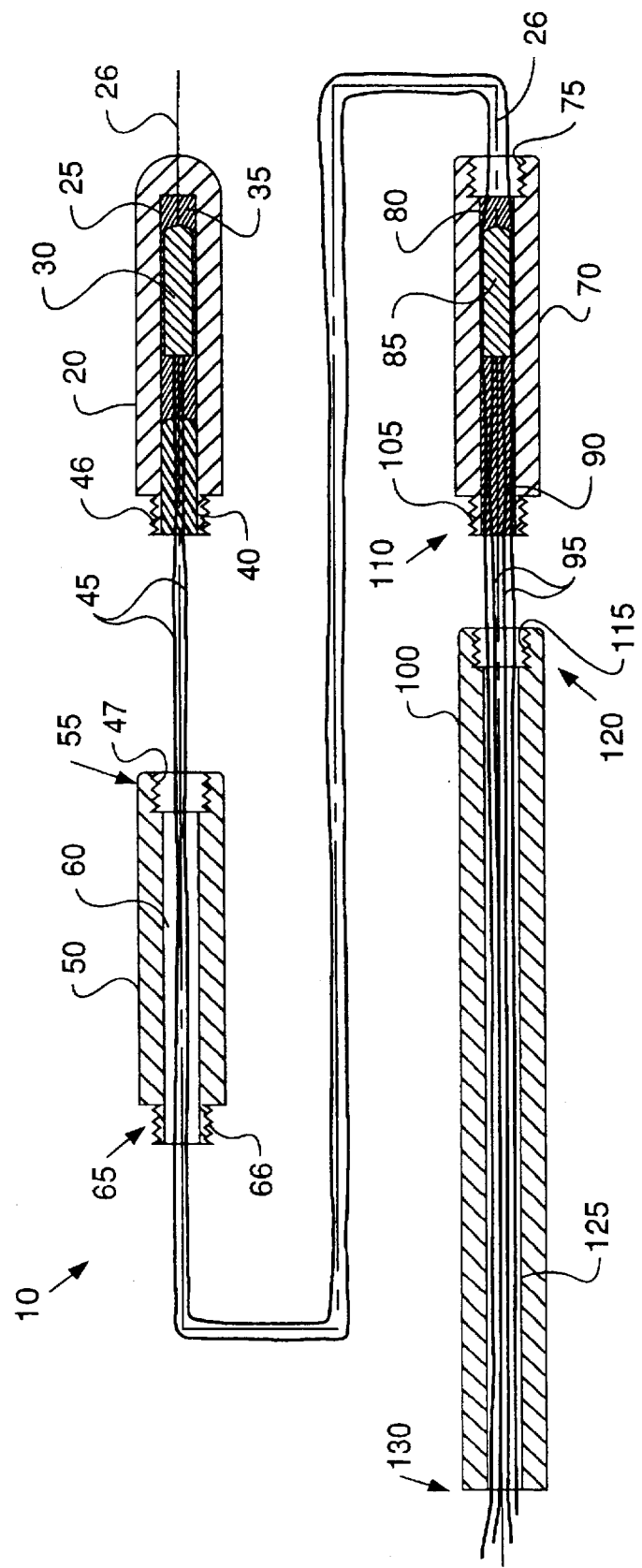
FIG. 1 generally shows a cross sectional schematic diagram of a preferred embodiment of the quench effectiveness probe of the present invention.

Referring to FIG. 1, a general cross sectional view of a preferred embodiment of the quench probe 10 of the present invention is shown. The quench probe 10 preferably includes two temperature sensors that vary their electrical resistance as a function of the temperature of the sensors 85, 30. In a preferred embodiment of the present invention, the sensors 85, 30 comprise resistance temperature detectors ("RTD" sensors), but other similar sensing devices could be readily and easily substituted for the RTD sensors 85, 30 without deviating from the scope of the present invention as defined by the appended claims. A preferred embodiment of the present invention includes two RTD sensors 85, 30 that are thermally isolated from one another by a heat resistive sheath 50. By thermally isolating the two RTD sensors 85, 30 the second RTD sensor 85 can measure an ambient quench temperature that is relatively unaffected by the heated first RTD sensor 30. In this manner, the probe 10 can measure a temperature differential between the first RTD sensor 30 and the second RTD sensor 85 and articulate a relative heat convection coefficient for the quench in the area of the probe 10. The quench probe 10 preferably includes a first heat conductive sheath 20 having a cavity 25 therein. In a preferred embodiment, the first conductive heat sheath is constructed from stainless steel. However, as will be appreciated by those skilled in the art, other materials could be readily and easily substituted and nevertheless remain within the scope of the present invention as defined by the appended claims. As shown in the figure, the cavity 25 preferably includes a longitudinal bore along a longitudinal axis 26 of the first heat conductive sheath 20. Installed within the cavity 25 is a first resistance temperature detector ("RTD") 30, which varies its resistance as a function of temperature. In the preferred embodiment, a 50 Ohm platinum RTD sensor is used for the first RTD. However, other similar sensors having different resistance values or constructed from different materials could readily and easily be substituted. The first RTD sensor 30 is preferably installed using thermally conductive epoxy 35 and the cavity 25 is then sealed using thermally insulating epoxy 40. Lead wires 45 extend from the first RTD sensor 30, through the thermally conductive epoxy 25 and the thermally insulating epoxy 40. As will be described in more detail below, lead wires 45 are connected to the first RTD sensor 30 and extend through the other components and exit from the probe through a thermally insulating sheath.

A first end 55 of a heat resistive sheath 50 is attached to the first heat conductive sheath 20. In a preferred embodiment, the first heat conductive sheath 20 includes a male threaded portion 46 and is attached to said heat resistive sheath 50 by connecting the threaded portion 46 to a reciprocal female threaded portion 47. As is shown in FIG. 1, the heat resistive sheath 50 includes a bore 60 through a longitudinal axis 26. Threaded through the bore 60 are the lead wires 45 from the first RTD sensor 30. A second end 65 of the heat resistive sheath 50 includes a male threaded portion 66. The second end of the heat resistive sheath 50 is attached to a second heat conductive sheath 70 and preferably is attached using the male threaded portion 66 and a reciprocal female threaded portion 75.

The second heat conductive sheath 70 is preferably constructed of stainless steel. However, other suitable heat conductive materials can be readily and easily substituted for the stainless steel while remaining within the spirit and scope of the present invention as defined by the appended claims. The second heat conductive sheath 70 preferably includes a longitudinal bore 80 along a longitudinal axis 26 of the sheath 70. A second RTD sensor 85 is preferably installed within the longitudinal bore 80 using an thermally conductive epoxy 90, although other heat conductive fastening materials could also be used. In a preferred embodiment, the second RTD sensor comprises a 100 ohm platinum RTD. However, other similar sensors having different resistance values or constructed from different materials could be readily and easily used without deviating from the scope of the present invention as defined by the appended claims. The lead wires 45 from the first RTD sensor 30 are threaded through the longitudinal bore 80 and around the second RTD sensor 85. A second set of lead wires 95 extend from the second RTD sensor 85. The second heat conductive sheath 70 is attached to a second heat resistive sheath 100. Preferably, the second heat conductive sheath 70 includes a male threaded portion 105 on an end 110 of the sheath 70. The sheath 70 is preferably attached to the second heat resistive sheath 100 using the male threaded portion 105 and a reciprocal female threaded portion 115 on an end 120 of said heat resistive sheath 100.

The second heat resistive sheath 100 preferably includes a longitudinal bore 125 parallel to a longitudinal axis of said sheath 100. The lead wires 45 and the second set of lead wires 95 are threaded through said bore 125 and extend out a second end 130 of said second heat resistive sheath 100.

As is described more fully below, in this preferred configuration, the second RTD sensor 85 measures an ambient temperature of the quench. The first RTD sensor 30 produces a known quantity of heat and the cooling effectiveness can therefore be measured by reading the temperatures of the first and second RTD, to determine the magnitude of the temperature increase caused by the known quantity of heat and the fluid heat transfer.

Figure 2:
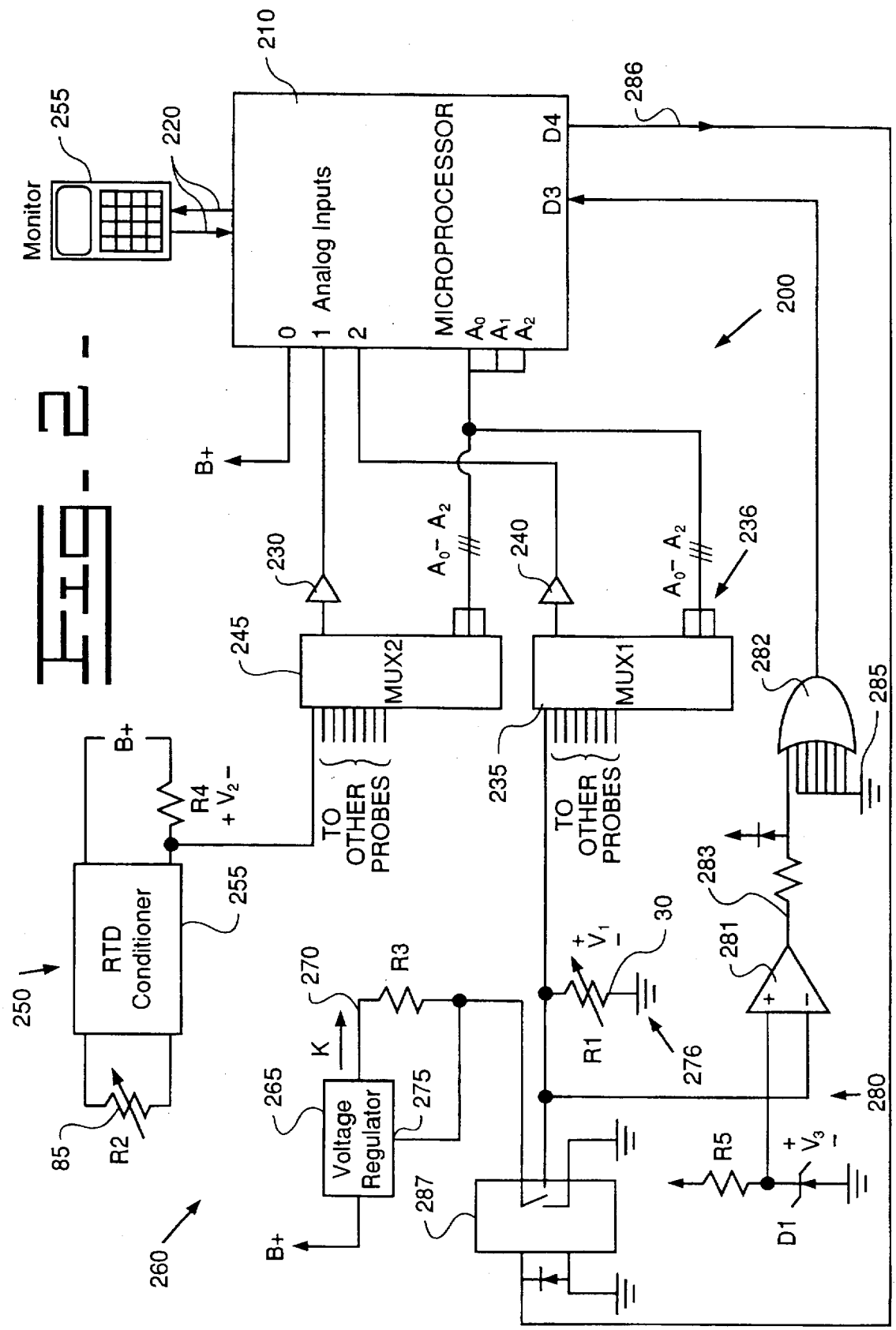
FIG. 2 generally shows a schematic diagram of a preferred embodiment of the heat treat quench monitoring and control circuitry included in an aspect of the present invention.

Referring now to FIG. 2, a preferred embodiment of a monitoring circuitry 200 used in connection with a preferred embodiment of the quench probe 10 is shown. The monitoring circuit 200 includes a microprocessor 210 which is electrically connected by communications channels 220 to a monitor 225 or other similar input and display device. The microprocessor used in a preferred embodiment is a Little Giant Model MKT1-LG-X, manufactured by Z-World Engineering located in Davis, Calif. However, other microprocessors or microcomputers with similar capabilities could be readily and easily substituted without deviating from the spirit and scope of the present invention as defined in the appended claims.

The microprocessor 210 includes at least two analog inputs, designated in the figure as analog inputs 1 and 2. The microprocessor also preferably includes a three bit address bus A0–A2. Additionally, the microprocessor 210 is connected to a power source designated in the figure as B+. The microprocessor 210 monitors the power source B+ to determine whether it is at a sufficient voltage level to power the circuit 200. If the voltage level of the power source B+ fails below a predetermined level, in a preferred embodiment 23.5 volts, then the microprocessor issues a warning over lines 220 to a monitor 225. As is known to those skilled in the art other signal and power conditioning circuitry is generally associated with the microprocessor and the power supply B+. However, since such circuitry is well known in the art and is readily and easily implemented it is not shown in FIG. 2.

Analog input 2 of the microprocessor 210 is connected to the output of a first buffer 240. The input of the first buffer 240 is connected to the output of a first multiplexer 235. The three address bits A0–A2 are connected to the address inputs 236 of the multiplexer 235. An eight channel multiplexer is shown in FIG. 2, and can be used simultaneously with up to eight quench probes of the type shown in FIG. 1. However, other multiplexers having either a greater number of channels or fewer channels could be readily substituted. As is known to those skilled in the art, the output of the multiplexer depends on the channel that is selected on the address bits A0–A2. Thus, the microprocessor 210 selects the channel that it desires to read on analog input 2 by sending a corresponding bit pattern on address lines A0–A2.

Likewise, analog input 1 of the microprocessor 210 is connected to the output of a second buffer 230. The input to the second buffer 230 is the output of a second multiplexer 245. The operation of the second multiplexer 245 is similar to that described above and will not be repeated here.

The second multiplexer 245 is connected to a second RTD sensor circuit 250 associated with the second RTD sensor 85. The resistance value of the second RTD sensor 85 is designated in FIG. 2 as R2. The second RTD sensor circuit 250 includes the resistance R2 of the second RTD sensor 85, an RTD conditioner circuit 255 (well known to those skilled in the art), a positive supply voltage B+, and a measuring resistor R4. As is known to those skilled in the art, the resistance of an RTD sensor varies with temperature; as the temperature of the sensor increases, its resistance likewise increases. In the second RTD sensor circuit 250, the voltage $V_2$ across the measuring resistor R4 is directly proportional to the resistance of the second RTD sensor 85. Thus, by measuring the voltage $V_2$ across resistor R4, the microprocessor 210 can calculate the temperature of the second RTD sensor 85. The microprocessor 210 inputs the voltage $V_2$ across the measuring resistor R4, through the second multiplexer 245, the buffer 230 and into the analog channel 1. In a preferred embodiment of the present invention the second RTD sensor 85 is used to measure an ambient temperature of the quench. Thus, the voltage level $V_2$ read into analog input 1 will represent the ambient quench temperature.

The temperature differential circuit 260 is connected to an input of the first multiplexer 235. The temperature differential circuit 260 includes a voltage regulator 265 which is connected to the power source B+. The voltage regulator 265 outputs a constant current K on an electrical connector 270 which is connected to a resistor R3. The current K is a function of the resistance value R3 and the voltage output of the voltage regulator 265. A high impedance return 275 is also connected to the resistor R3. The resistance of the first RTD sensor 30 is represented by R1. The first RTD sensor 30 is connected to the resistor R3, to the high impedance return 275 and to ground 276. The voltage drop across the first RTD sensor 30 is determined by the resistance R1 of the sensor. Because the current flowing through the resistor R1 is a constant K the voltage drop $V_1$ across the resistor R1 is proportional to the resistance. Thus, the temperature of the first RTD 30 is a function of the voltage drop $V_1$.

As is known to those skilled in the art, an RTD sensor can be heated by applying electrical current to it. Thus, the first RTD sensor 30 will produce a fixed quantity of heat as a result of the constant current K that is applied. The temperature of the first RTD sensor 30 is then a function of several factors which are known: the ambient temperature of the quench, the heat produced by the first RTD, the resistance of the first RTD, and the conduction coefficient of the probe. By knowing these values, the cooling effectiveness of the quench can be readily and easily calculated.

In another aspect of a preferred embodiment of the present invention a safety shut-off circuit 280 is provided to prevent the first sensor 30 from overheating. The amount of heat generated by the first sensor 30 is a function of the applied constant electrical current K, the sensor resistance R1, fluid heat capacity, and fluid flow rate of the quench system. Quench media having high fluid convection potential will remove heat from the sensor more effectively and will, therefore, reduce the maximum temperature the first sensor 30 can reach. To allow cooling effectiveness measurements of such high convection quench media, the heat generated by the first sensor 30 must be relatively large. If such a sensor was accidentally placed in a low convection media such as air or was accidentally removed from the quench system, the generated heat could damage or destroy the first sensor 30. Consequently, an automatic shut-off circuit 280 is preferably included to help ensure continued sensor integrity and allow measurements of high convection quench media.

The measurement system of the present invention may be used with quench systems having a wide range of different convection capabilities by simply substituting a different value resistor R3, which adjusts the maximum heat output of the first sensor 30. As would be apparent to those skilled in the art, a resistor R3 of higher resistance will cause the first sensor to produce less heat than a lower resistance value. Although the resistor R3 shown in FIG. 3 has a fixed value, it is apparent to those skilled in the art that a variable resistance device could be substituted so that the resistance R3 could be easily changed and the system 200 could be more easily modified for different quench media.

The shut-off circuit 280 monitors the voltage V1 across the first sensor 30 and sends a signal to the microprocessor 210 if V1 exceeds a predetermined voltage limit. Since V1 is directly proportional to the temperature of the first sensor 30, a limit on V1 translates into a limit on the temperature of the heated sensor.

The shut-off circuit 280 is connected to a digital input D3 on the microprocessor 210. The circuit 280 includes a voltage comparator 281 which compares the voltage across the first sensor V1 with the voltage V3 across a zener diode D1. As is known to those skilled in the art, the value of the zener diode D1 establishes the voltage level V3 which, in turn, is an input to the comparator 281. The output 283 of the comparator is connected to the input of a multiple input OR gate 282. When the output 283 of the comparator 281 goes HIGH, it indicates that the voltage level V1 exceeds the predetermined voltage level V3 established by the zener diode D1. In a preferred embodiment, the OR gate 282 shown will accommodate up to eight probes, with any unused inputs connected to ground 285. If any of the inputs to the gate 282 are HIGH, the output of the gate 282 is also HIGH. When the output 283 of the comparator 282 goes HIGH it causes the output of the OR gate 282 to go HIGH, thereby indicating an overtemperature condition to the microprocessor 280. When the microprocessor 210 receives the HIGH signal from the OR gate 282, it produces an overtemperature signal 286 on the digital output D4. The over temperature signal energizes the relay 287, and the first sensor 30 is disconnected from the constant current source 287, protecting it from overheating damage. Once the relay 287 is energized, the microprocessor 210 waits for a user input on the monitor and input device 255 before resetting the relay 287 and reconnecting the first sensor 30 to the constant current source.

Referring now to FIG. 3, a flowchart illustrating a computer software program for implementing a preferred embodiment of the present invention is shown. The program depicted in this flowchart is particularly well adapted for use with the Little Giant microprocessor and associated components described above, although any suitable microprocessor may be utilized in practicing an embodiment of the present invention. These flowcharts constitute a complete and workable design of the preferred software program, and have been reduced to practice on this microprocessor system. The software program may be readily coded from these detailed flowcharts using the instruction set associated with this system, or may be coded with the instructions of any other suitable conventional microprocessors. The process of writing software code from flowcharts such as these is a mere mechanical step for one skilled in the art.

In block 300, the software routine begins. Program control passes to block 310 where the microprocessor 210 reads the voltage level $V_2$ across the resistor R4, which is proportional to the resistance R2 of the second RTD sensor 85. Program control then passes to block 320 where the microprocessor 210 calculates an ambient temperature of the quench. The ambient temperature of the quench is proportional to the voltage $V_2$. In a preferred embodiment, the voltage level is scaled according to the following equation:

$$T_{amb} = 6250 \left( \frac{V_2}{205} \right) - 25$$

where $T_{amb}$ is the ambient temperature of the quench.

Program control passes from block 320 to block 330. In block 330, the microprocessor 210 reads the voltage level $V_1$ across the resistor R1 of the first RTD sensor 30. Program control then passes to block 340. In block 340, the microprocessor 210 calculates the resistance value R1 according to the following equation:

$$R_1 = V_1/K$$

where K is the constant current output from the voltage regulator 265.

Program control passes to block 350 where the microprocessor calculates the temperature of the first RTD sensor 30. Using scaling values of the specific RTD sensor, a preferred embodiment uses the following equation:

$$T_{HTR} = \frac{R_1 - 50}{50(0.00385)}$$

where $T_{HTR}$ is the temperature of the first RTD sensor 30.

Program control then passes to block 360, where the microprocessor calculates the electrical power that is consumed, and therefore mined into heat, by the first RTD sensor 30. The following well known equation determines the power consumption of the RTD:

$$q = K(V_1)$$

where K is the constant current output from the voltage regulator 265, and $V_1$ is the measured voltage drop across the resistor R1.

Program control then passes to block 370 where the microprocessor 210 calculates the convection coefficient of the quench. In a preferred embodiment, the microprocessor 210 uses the following equation:

$$h = \frac{1/A}{\left( \frac{T_{HTR} - T_{AMB}}{q} - 1.4932 \right)}$$

where A is the surface area of the first heat conductive sheath 20 over the length of the first RTD sensor 30; and 1.4932 is a conductive factor to account for heat losses between the surface of the first RTD sensor 30 and the surface of the first heat conductive sheath 20.

Program control then passes to block 380 where the microprocessor compares the calculated convection coefficient h to a predetermined value or values. Program control then passes to block 390. If the calculated convection coefficient h is outside a desired range as determined by the predetermined values, then the microprocessor will provide a signal on lines 220 to the monitor.

Although a preferred embodiment has been described herein with reference to a single probe 10 used with the monitoring of circuit 200, those skilled in the art will recognize that there is no limit on the number of probes that can be used. In FIG. 2, for example, the circuit 200 can accommodate up to eight probes 10. These probes would presumably be placed in different locations throughout the quench system to obtain more localized readings and measurements about quench cooling effectiveness. For example, at least one probe may be located at the flow inlet and could readily determine any change to inlet flow due to restriction, blockage or mechanical failure while other probes could be located in other areas of the quench system.

We claim:

1. An apparatus for measuring the cooling effectiveness of a quench, comprising, in combination:

a first heat conductive sheath having a cavity therein;

a first temperature sensor installed in said cavity of said first heat conductive sheath, said first temperature sensor being heated by passing a constant current there through;

a second heat conductive sheath having a cavity therein;

a second temperature sensor installed in said cavity of said second heat conductive sheath, said second temperature sensor measuring the ambient quench temperature; and a heat resistive sheath installed between said first and second heat conductive sheaths substantially collinear with said first and second heat conductive sheaths.

2. An apparatus according to claim 1, wherein said first and second temperature sensors have a variable electrical resistance and said electrical resistance of said first temperature sensor is a function of a temperature of said first sensor, and said electrical resistance of said second sensor is a function of a temperature of said second sensor.

3. An apparatus according to claim 2, wherein said first and second temperature sensors include RTD sensors.

4. An apparatus according to claim 1, including:

a microprocessor, wherein said microprocessor causes said first temperature sensor to produce heat, measures a first temperature of said first temperature sensor, measures a second temperature of said second temperature sensor, and calculates cooling effectiveness as a function of a difference between said first and second temperatures.

5. An apparatus according to claim 2, including:

a microprocessor, wherein said microprocessor causes said first temperature sensor to produce heat, measures a first temperature of said first temperature sensor, measures a second temperature of said second temperature sensor, and calculates cooling effectiveness as a function of a difference between said first and second temperatures.

6. An apparatus according to claim 5, wherein said first and second temperature sensors include RTD sensors.

7. An apparatus according to claim 1, wherein said first temperature sensor is installed in said cavity of said first heat conductive sheath using a thermally conductive epoxy and said second temperature sensor is installed in said cavity of said second heat conductive sheath using thermally conductive epoxy.

8. An apparatus according to claim 1, wherein a thermally insulating epoxy is installed in a portion of said cavity of said second heat conductive sheath.

9. An apparatus according to claim 7, wherein a thermally insulating epoxy is installed in a portion of said cavity of said second heat conductive sheath.

10. An apparatus according to claim 6, wherein said first and second RTD sensors comprise platinum RTD sensors.

11. An apparatus according to claim 1, including a second heat resistive sheath attached to said second heat conductive sheath.

12. An apparatus according to claim 11, wherein said heat resistive sheath and said second heat resistive sheath are constructed from at least 30% glass filled polyetheretherketone.

13. An apparatus according to claim 1, wherein said heat resistive sheath is threadably attached to said first heat conductive sheath and to said second heat conductive sheath.

14. An apparatus according to claim 11, wherein said heat resistive sheath is threadably attached to said first heat conductive sheath and said second heat conductive sheath and said second heat resistive sheath is threadably attached to said second heat conductive sheath.

15. An apparatus according to claim 4, including a monitor connected to said microprocessor.

16. An apparatus according to claim 6, including a first conditioning circuit associated with said first RTD sensor and a second conditioning circuit associated with said second RTD sensor.

17. An apparatus according to claim 16, wherein said second conditioning circuit includes constant current means for providing a known constant current to said first RTD sensor.

18. An apparatus according to claim 17, wherein the microprocessor calculates the heat output of the first RTD sensor according to the following formula:

$$h = \frac{1/A}{\left(\frac{T_{HTR} - T_{AMB}}{q} - B\right)}$$

where A is the surface area of the first heat conductive sheath over the length of the first RTD sensor;

$T_{HTR}$ is the temperature of the first temperature sensor;

$T_{AMB}$ is the temperature of the second temperature sensor;

q is the power consumption of the first temperature sensor;

h is the convection coefficient of the first temperature sensor; and

B is a conductive factor to account for heat losses between the surface of the first RTD sensor and the surface of the first heat conductive sheath.

19. An apparatus according to claim 17, wherein said second conditioning circuit includes a multiplexer connected between the microprocessor and said second RTD sensor.

20. An apparatus according to claim 5, including a shut-off circuit electrically connected to said first temperature sensor and to said microprocessor.

21. An apparatus according to claim 20, wherein said shut-off circuit produces an overtemperature signal when said first temperature is greater than a first predetermined temperature.

22. A method of operating an apparatus for monitoring the effectiveness of a quench, said method comprising the steps of:

measuring a first temperature of a first temperature sensor; measuring a second temperature of a second second sensor; causing said first temperature sensor to produce heat; and calculating the convection coefficient of said quench.

23. A method according to claim 22, wherein said first and second temperature sensors are RTD sensors.

24. A method according to claim 23, wherein said step of causing said first temperature sensor to produce heat includes the step of applying a known electrical current to said first temperature sensor.

25. A method according to claim 24, including a step of calculating a heat output of said first temperature sensor.

26. A method according to claim 22, wherein said step of measuring the temperature of said first and second temperature sensors, includes the step of measuring a resistance of said first and second RTD sensors, measuring the voltages across said first and second RTD sensors, and calculating a first and second temperature of said first and second RTD sensors.

27. A method according to claim 26 including the step of comparing said first temperature to a predetermined temperature, and disabling said monitoring apparatus in response to said first temperature exceeding said predetermined temperature.

* * * * *